United States Patent
Lee et al.

(10) Patent No.: US 7,033,476 B2
(45) Date of Patent: *Apr. 25, 2006

(54) SEPARATION AND COUNTING OF SINGLE MOLECULES THROUGH NANOFLUIDICS, PROGRAMMABLE ELECTROPHORESIS, AND NANOELECTRODE-GATED TUNNELING AND DIELECTRIC DETECTION

(75) Inventors: James W. Lee, Oak Ridge, TN (US); Thomas G. Thundat, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 496 days.

This patent is subject to a terminal disclaimer.

(21) Appl. No.: 10/335,475

(22) Filed: Dec. 31, 2002

(65) Prior Publication Data

US 2004/0124084 A1    Jul. 1, 2004

(51) Int. Cl.
*G01N 27/453* (2006.01)
(52) U.S. Cl. ................... 204/603; 204/601; 204/600
(58) Field of Classification Search ............ 204/451, 204/452, 601, 603, 600
See application file for complete search history.

(56) References Cited

U.S. PATENT DOCUMENTS

| 6,447,663 | B1 | 9/2002 | Lee |
| 6,905,586 | B1 * | 6/2005 | Lee et al. ............ 204/600 |

* cited by examiner

*Primary Examiner*—Alex Noguerola
(74) *Attorney, Agent, or Firm*—James M. Spicer

(57) ABSTRACT

An apparatus for carrying out the separation, detection, and/or counting of single molecules at nanometer scale. Molecular separation is achieved by driving single molecules through a microfluidic or nanofluidic medium using programmable and coordinated electric fields. In various embodiments, the fluidic medium is a strip of hydrophilic material on nonconductive hydrophobic surface, a trough produced by parallel strips of hydrophobic nonconductive material on a hydrophilic base, or a covered passageway produced by parallel strips of hydrophobic nonconductive material on a hydrophilic base together with a nonconductive cover on the parallel strips of hydrophobic nonconductive material. The molecules are detected and counted using nanoelectrode-gated electron tunneling methods, dielectric monitoring, and other methods.

38 Claims, 12 Drawing Sheets

SEPARATION AND COUNTING OF SINGLE MOLECULES THROUGH NANOFLUIDICS, PROGRAMMABLE ELECTROPHORESIS, AND NANOELECTRODE-GATED TUNNELING AND DIELECTRIC DETECTION

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

BACKGROUND OF THE INVENTION

1. Field of the Invention

The invention relates to the separation, detection and counting of single molecules at nanometer scale. More particularly, molecular separation is achieved by driving single molecules through a microfluidic or nanofluidic medium using programmable and coordinated electric fields, and detecting the molecules using nanoelectrode-gated tunneling methods, dielectric monitoring and other methods.

2. Background Information

A key step in the invention is the ability to fabricate a required nanometer-scale gap that is defined as the distance between a pair of sharp nanoelectrode tips. Such a gap is used in the present invention as a molecular detection gate. The following is a description of our recent invention, now U.S. Pat. No. 6,447,663, issued Sep. 10, 2002, for accomplishing the construction of such a nanogap.

Nanometer-scale modification of nanostructures can be carried out in liquids at ambient temperature and neutral pH through electric field-directed, programmable, pulsed electrolytic metal deposition or depletion. The use of pulsed current is a critical feature in the method, while temperature and pH are not critical parameters.

A programmable and short (time scale of nanoseconds to milliseconds) pulsed direct current source is used to control the number of atoms being deposited by the electrolytic metal reduction and deposition process. As shown in the following platinum deposition reaction at a cathode using water-soluble hexachloroplatinate, the number of electrons supplied can control the formation of metallic platinum. In electrolytic deposition, electric current and the duration of the current can control the number of electrons.

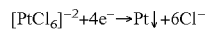

$$[PtCl_6]^{-2} + 4e^- \rightarrow Pt\downarrow + 6Cl^-$$

Other water-soluble metal compounds that have been shown to be applicable include, but are not limited to, the following: $PtCl_4$, $OsCl_3$, $Na_2[PtCl_6]$, $Na_2[OsCl_6]$, $(NH_4)_2RuCl_6$, $K_3RuCl_6$, $Na_2PdCl_6$, $Na_2IrCl_6$, $(NH_4)_3IrCl_6$, $(NH_4)_3RhCl_6$, $K_2PdCl_4$, $(NH_4)_2PdCl_4$, $Pd(NH_3)_4Cl_2$, $ReCl_3$, $NiCl_2$, $CoCl_2$, $PtO_2$, $PtCl_2$, $Pt(NH_3)_4Cl_2$, $CuSO_4$, $(NH_4)_6Mo_7O_{24}$, $NaAuCl_4$, $K_2[PtCl_4]$, and $K_3Fe(CN)_6$. Combinations of two or more water-soluble metal compounds can be used sequentially or simultaneously.

As illustrated in FIG. 1, an embodiment of our recent invention involves a special utilization of a programmable current source 18 that can precisely control the number of electrons used to achieve the desired nanometer-scale electrolytic metal deposition. A nonconductive substrate 10 supports nanometer-sized electrodes in the form of a cathode 12 and anode 14 (also called nanowires and nanoelectrodes), which are usually comprised of gold but can be other metals or conductive materials. For example, if especially sharp nanoelectrode tips are desired, a harder, more stable metal such as platinum or palladium can be deposited. Spacing between the nanoelectrode tips 13, 15 in the range of 1 nm to 10 µm produces good results.

In FIG. 1, a preselected metal 16 is deposited onto the tip of the cathode nanoelectrode 12. The metal 16 is usually platinum (Pt), but can be any metal that can be deposited electrolytically. The programmable, pulsable current source 18 has electrical leads 20, 22 to the respective nanoelectrodes 12, 14. A bypass circuit 24, which includes a bypass selector switch 26 and a variable resistor 28, is also shown.

The nanoelectrodes 12, 14 represent a subset of microscopic sized structures (nanostructures) that are suitable for use. Nanostructures acting as electrodes can be of various sizes and shapes. Spacing between the two nanostructures should not exceed 50 µm. Preferably, the spacing is 20 µm or less, more preferably 10 µm or less, and most preferably, 1 µm or less.

The programmable, pulsable current source 18 can be of any suitable construction. Keithley Model 220 programmable current source or the latest Keithley Model 2400 series of Source Meters (available from Keithley Instruments, Inc., 28775 Aurora Road, Cleveland, Ohio 44139, or on the Internet at www.keithley.com) are already capable of supplying a minimum of about 9400 electrons per pulse [500 fA×3 ms×electron/(1.60×10$^{-19}$ C)]. This could translate to a deposition of 2350 platinum atoms per pulse based on the stoichiometry of the deposition reaction. If this amount of platinum is deposited on the end of a nanowire with a 10- by 10-nm cross section, 2350 platinum atoms per pulse can translate into about 1 nm of metal deposition (2.6 layers of platinum atoms) per pulse. The programmable, pulsable current source 18 should be capable of controlling the process so that nanometer metal deposition or depletion as precise as about 1500 metal atoms per pulse can be achieved. A preferable range is contemplated to be 1500 to $10^{14}$ atoms per pulse, although operation is possible well beyond this range.

The bypass circuit 24 is preferably added to fine-tune the electron flow for even more precise control of the deposition or depletion, i.e., the addition or removal of monolayers or submonolayers of atoms. The bypass circuit 24 is used to divert some of the electricity away from the nanoelectrodes 12, 14 in order to deposit (or deplete) fewer metal atoms per pulse. For example, when the impedance of the variable resistor 28 is adjusted to 50% of the impedance between the two nanoelectrodes 12, 14, two thirds of the 9400 electrons per pulse can be drained through the bypass circuit 24. In this case, the electrolytic metal deposition can be controlled to a step as precise as 780 platinum atoms (3130 electrons) per pulse. This translates to a deposition of 0.87 layer of platinum atoms 16 on a 10- by 10-nm surface at the tip of the cathode nanoelectrode 12. By allowing a greater portion of the current to flow through the bypass circuit 24, it is possible to control deposition of metal 16 atoms as precisely as 100 atoms per pulse. A preferable range for this extremely finely controlled deposition is contemplated to be 100–2500 atoms per pulse, although operation is possible well beyond this ultrafine deposition range.

The bypass circuit 24 can also protect the nanometer structure from electrostatic damage, especially when the structure is dry. For example, after desired programmable electrolytic metal deposition is achieved as illustrated in FIG. 1, the bypass circuit 24 should remain connected with the nanostructures 12 and 14 while the programmable pulsing current source can then be removed. As long as the bypass circuit remains connected with the nanostructures 12 and 14, any electrostatic charges that might be produced during wash and dry of the nanostructures will be able to flow through the bypass circuit 24. The bypass circuit 24 comprises the closed switch 26, the variable resistor 28, and wire leads that connect the switch 26 and the variable resistor 28 with the nanoelectrodes 12, 14. This prevents accumulation of electrostatic charges at any one of the electrodes against the other electrode from occurring, thus eliminating the possibility of electrostatic damage at the nanometer gap between the tips 13, 15 of the nanoelectrodes 12, 14.

A special nanostructural arrangement can be used to control the initiation point(s) of nanometer bonding. Special structural arrangements of the nanowire electrodes can now be made by various lithographic techniques to control the initiation point(s) of the electrolytic metal deposition. As shown in FIG. 2, multiple nanowire cathodes 12, 12' should have respective tips 13, 13' pointing to the respective tips 15, 15' of nanoelectrode anode 14 so that the strongest electric field is therebetween. Spacing of the multiple nanowire cathodes 12, 12' should be regulated to ensure deposition of metal 16, 16' at the desired cathode location, because the electric field (E) is a vector that is strongly dependent on distance (r):

$$E \propto r^{-2}.$$

In FIG. 3, electrolytic metal-dissolving reactions are applied to deplete metal, that is, to open nanometer gaps and control gap size. By conducting the reversal of the metal deposition reaction with sodium chloride solution instead of hexachloroplatinate as an electrolytic substrate, metallic platinum at the nanoelectrode anode tip 16 can be electrolytically depleted via dissolution in a controllable way according to the following reaction:

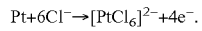

$$Pt + 6Cl^- \rightarrow [PtCl_6]^{2-} + 4e^-.$$

This metal-dissolution reaction should also be able to control the gap size between the nanoelectrode tips 13, 15. The site and the extent of electrolytic metal depletion can also be controlled by proper selection of the desired polarity of the electric field and by use of a programmable current source with a bypass circuit, as described herein.

The salient features, as described hereinabove, may be applied in full, in part, or in any combination. Any number of nanostructures can be simultaneously bonded or dissolved on a particular substrate. The nanostructure to be metal-deposited does not have to be metal. Any conductive nanowires such as, for example, nanotubes (especially carbon nanotubes), can be connected because of their capability for nanometer electrolytic metal deposition. For metal depletion, the nonmetallic ions do not have to be Cl⁻. Any anions, such as $F^-$ and $CN^-$, that can electrolytically dissolve metals (Pt, Pd, Au, etc.) may be used as alternative versions.

The above description is from our recently filed patent application entitled "Programmable Nanometer-Scale Electrolytic Metal Deposition and Depletion"; by James W. Lee and Elias Greenbaum; now U.S. Pat. No. 6,447,663; issued Sep. 10, 2002.

BRIEF SUMMARY OF THE INVENTION

In accordance with one aspect of our present invention, we provide an apparatus for the separation, detection and counting of single molecules in a liquid at nanometer scale that includes a base; a pair of macroelectrodes located on the base; means for accommodating the liquid, the means for accommodating the liquid located on the base between the macroelectrodes; a pair of nanoelectrodes located on the base crosswise of the means for accommodating the liquid, the gap between the nanoelectrodes forming a nanoscale detection gate, the nanoscale detection gate located in the liquid; a programmable pulse generator connected to produce an electrophoresis electric field between the macroelectrodes, the electrophoresis electric field capable of controllably moving molecules in the liquid along the means for accommodating a liquid through the detection gate; a pair of parallel spaced-apart electrically conductive plates, the base located between the parallel spaced-apart electrically conductive plates; a second programmable pulse generator connected to produce a holding electric field between the electrically conductive plates, the holding electric field capable of holding and/or orienting molecules in the liquid with respect to the base; and a molecule detection means connected to the nanoelectrodes.

In accordance with another aspect of our invention, the base has a nonconductive hydrophobic surface, and the means for accommodating the liquid is a strip of hydrophilic material on the nonconductive hydrophobic surface.

In accordance with another aspect of our invention, the base is a hydrophilic base, and the means for accommodating the liquid is a trough produced by two parallel strips of hydrophobic nonconductive material on the hydrophilic base.

In accordance with yet another aspect of our invention, the base is a hydrophilic base, and the means for accommodating the liquid is a covered passageway produced by two parallel strips of hydrophobic nonconductive material on the hydrophilic base along with a nonconductive cover on the parallel strips of hydrophobic nonconductive material.

DETAILED DESCRIPTION OF THE INVENTION

Figure 1:
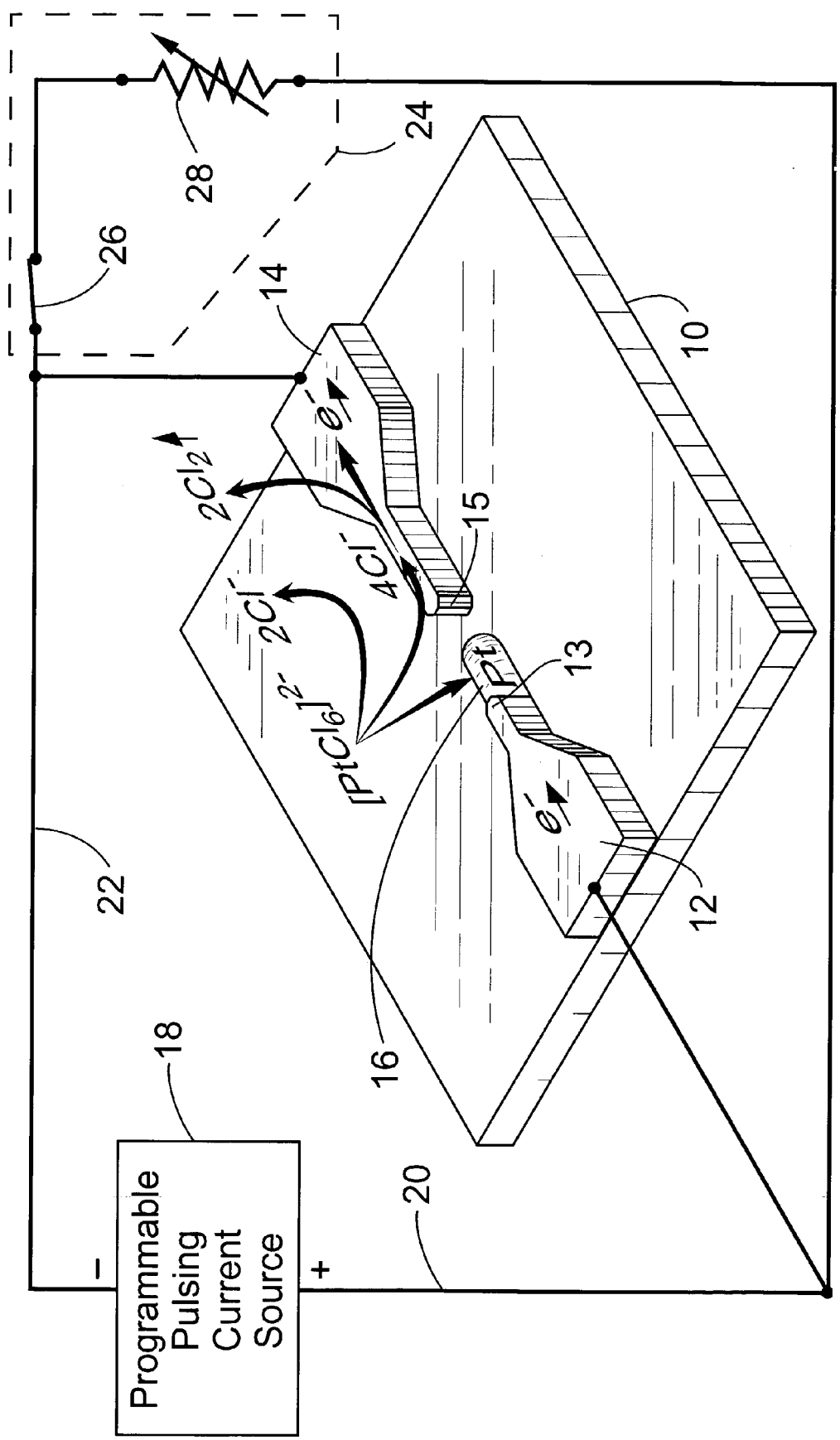
FIG. 1 is an illustration of nanogap manipulation through precision electrolytic deposition of platinum (Pt) on a gold nanostructure.
Figure 2:
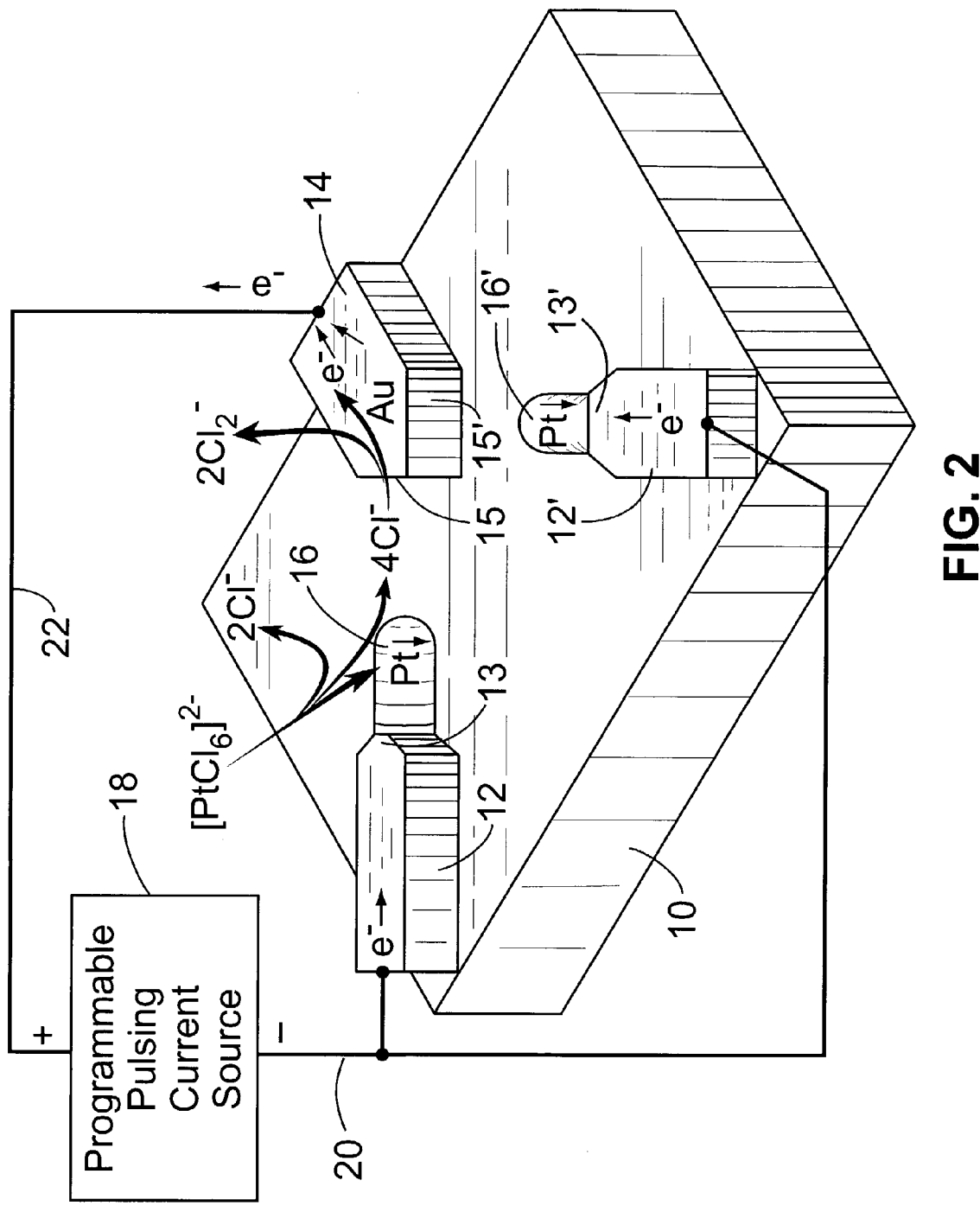
FIG. 2 is an illustration of nanogap modification through deposition of platinum on multiple gold nanostructures.
Figure 3:
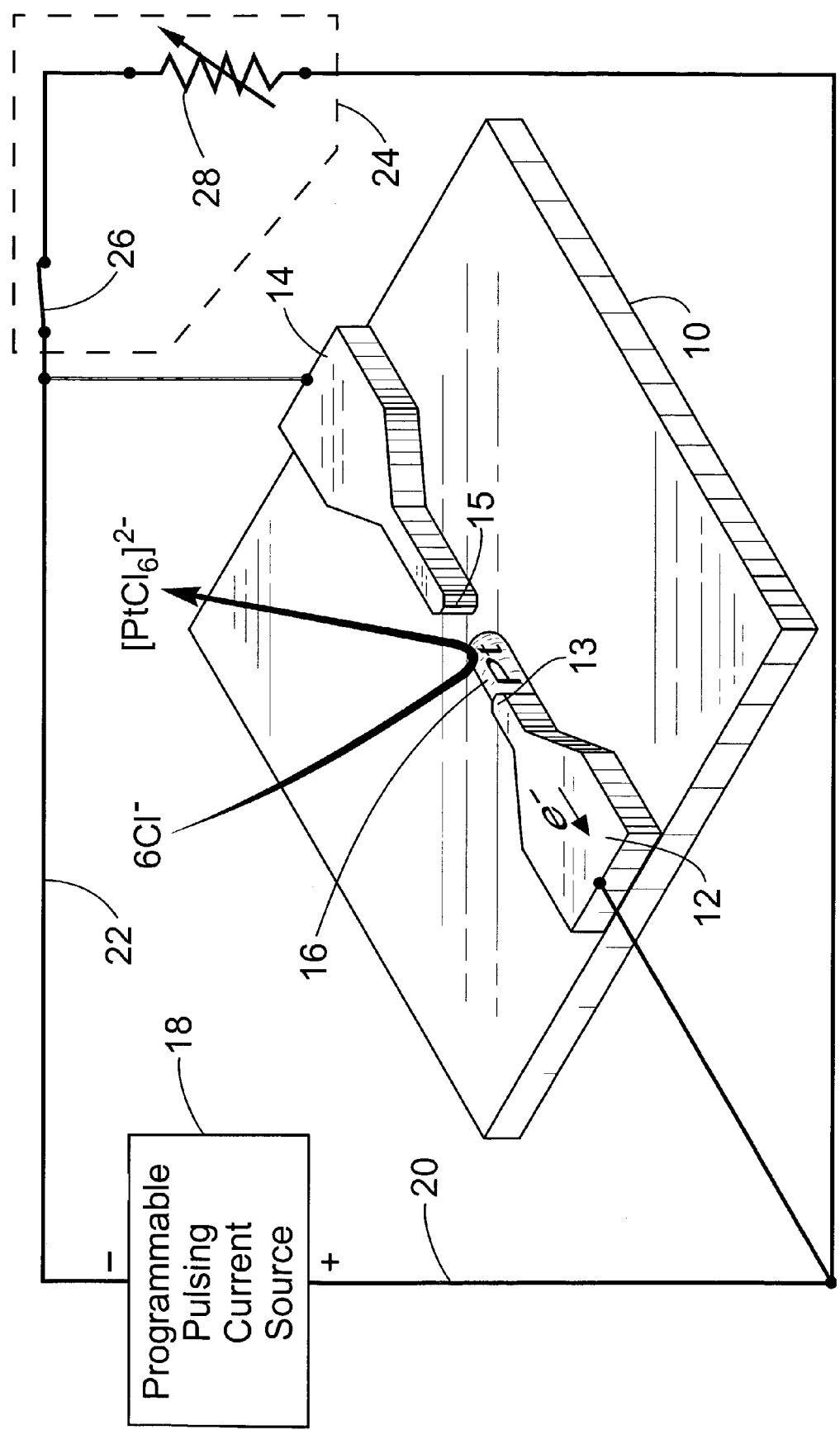
FIG. 3 is an illustration of nanogap modification through depletion of platinum from a gold nanostructure.

The invention is an apparatus and associated method for the separation, detection and counting of single molecules. These can include, but are not limited to, ions (such as $Mg^{2+}$, $Ca^{2+}$, $[PO_4H]^{2-}$, and $[Fe(CN)_6]^{3-}$), nucleic acids, proteins, and charged particles and molecules. In a first embodiment of the invention, the apparatus comprises three major parts: (1) a thin liquid layer, called a microfluidic or nanofluidic separation column, comprising a nanometer-thin layer of water or other suitable liquid maintained on a strip of solid hydrophilic supporting surface; (2) a molecular detection system capable of detecting single molecules through nanoelectrode-gated tunneling and dielectric measurements; and (3) a programmable electric field system for precisely controlling the movement of the sample molecules through the separation column and a detection gate.

In a first embodiment of the invention, shown in FIGS. 4–7, the separation and counting of single molecules is achieved by electrophoresizing sample molecules (SM) 47 through a thin liquid layer 48, also called a micro/nanofluidic separation column. The molecules 47 are detected at a nanoscale gate (nanogate) 42 using nanoelectrode-gated tunneling conductance spectroscopic measurements 65 and/or nanoelectrode-gated dielectric measurements 66. Consequently, the number of sample molecules 47 can be counted one by one as each of them passes through the detection gate 42. In this embodiment, an AFM and/or EFM probe 78 (FIG. 5) can easily be added at the nanoelectrode gate 42 as an optional means for molecular detection and/or counting.

Figure 4:
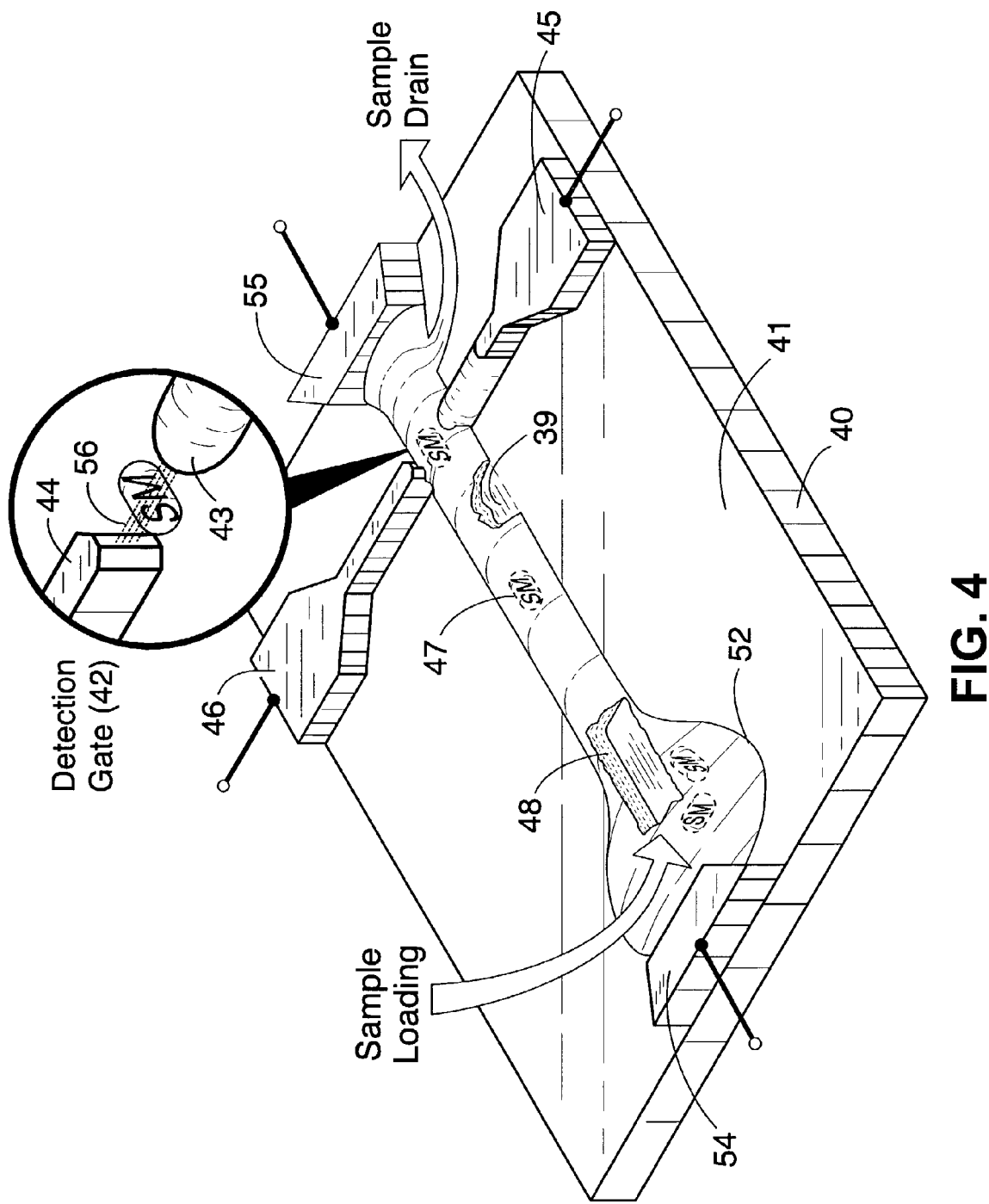
FIG. 4 illustrates part of a first embodiment of a molecular separation and counting system according to the invention. It features a substrate having a hydrophilic nonconductive strip between two electrophoresis electrodes on a hydrophobic surface, and a pair of molecular detection nanoelectrodes crosswise of a nanofluidic molecular separation column formed on the hydrophilic nonconductive strip.
Figure 5:
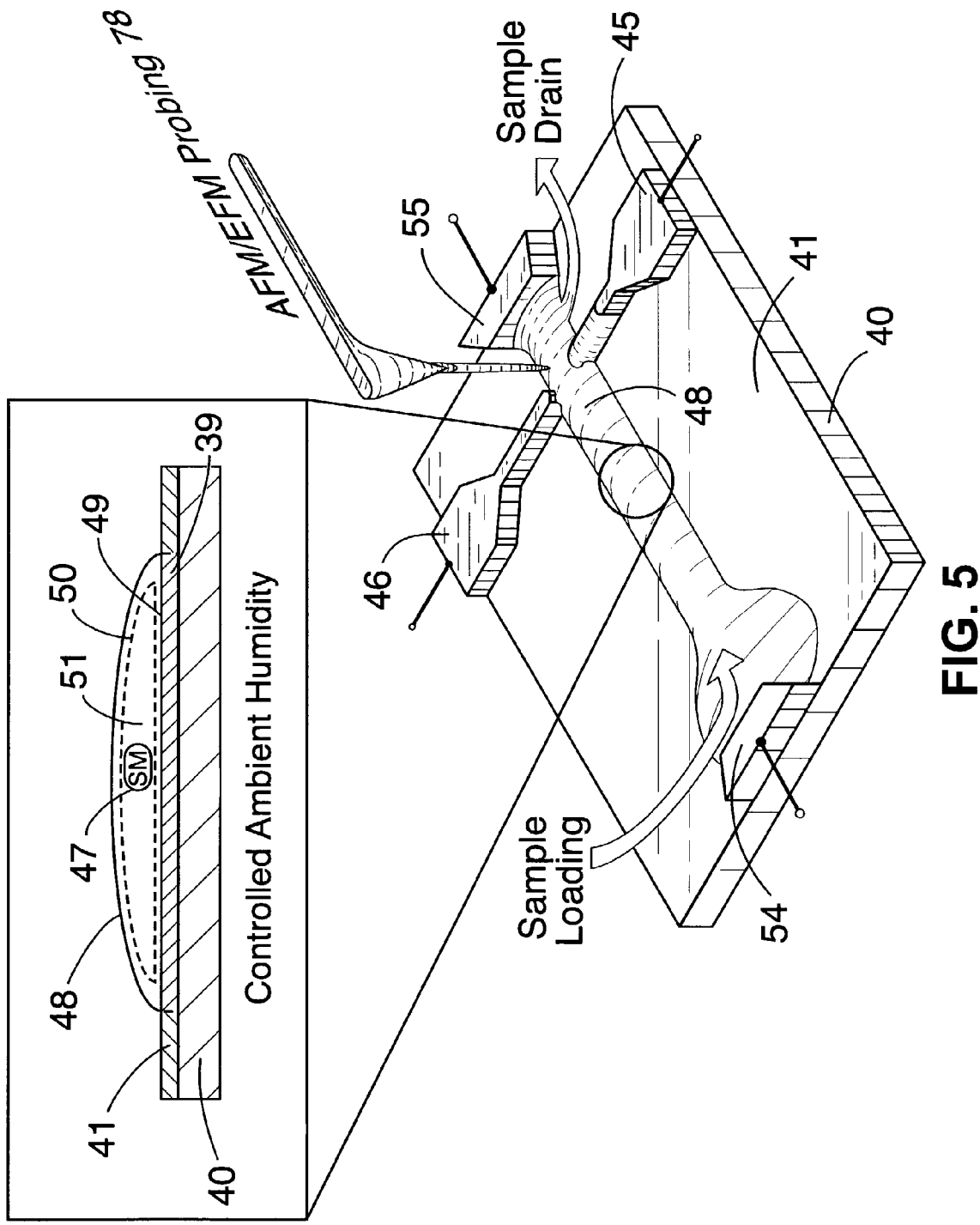
FIG. 5 is an illustration of a controlled micro/nanofluidic separation column (i.e., liquid column) that is produced on the hydrophilic strip (or line) of FIG. 4.

In this embodiment, the entire process including the loading, separation, and detection and or/counting of single molecules through the nanogate 42 is carried out on the surface of the substrate 40. In all embodiments of the invention, the substrate is any suitable material or sample plate, and is referred to generally as the base. FIGS. 4 and 5 particularly illustrate the thin liquid layer or micro/nanofluidic separation column 48 used for sample loading and separation in this first embodiment. In these figures, the substrate 40 is provided with a nonconductive hydrophobic surface 41, e.g., SiN, or a hydrogen-terminated Si surface. A nanometer-thin hydrophilic strip of material (e.g., SiO$_2$) 39 is produced in or on the hydrophobic surface 41 of the substrate 40. By producing and maintaining a thin liquid layer (micro/nanofluidic column 48) on the nanometer-thin strip of hydrophilic material 39, sample molecules 47 can be loaded into the thin liquid layer 48. Here, they are separated and then fed into the detection gate 42 (defined by the pair of nanoelectrodes 45, 46) for molecular detection and counting. The micro/nanofluidic molecular separation process is thus facilitated using the nanometer-thin liquid layer or column 48. The thin liquid layer can be formed, for example, by vapor such as water or electrolyte solution condensed on the hydrophilic strip 39 in a controlled-humidity environment.

It is noted, for example, that the hydrophilic strip 39 can have an optional expanded portion (region 52 nearest the macroelectrode 54 in FIG. 4). The expanded region 52 acts as a sample loading area which facilitates micro- or nanofluidic injection or micropipetting of the sample molecules 47 into the sample loading portion 52 of the liquid column 48. Likewise, an expanded area (not shown) in the drain region near the macroelectrode 55 will make the sample removal more convenient. Depending on the properties of a given sample molecule, sample loading and/or removal can be facilitated by the use of a micro/nanometer tip such as the tip of a cantilever. For example, a positively charged cantilever tip can be used to electrostatically pick up negatively charged sample molecules such as polynucleotides, and then transfer them into the loading zone where the sample molecules can be released from the tip by switching the tip voltage from positive to negative.

Figure 6:
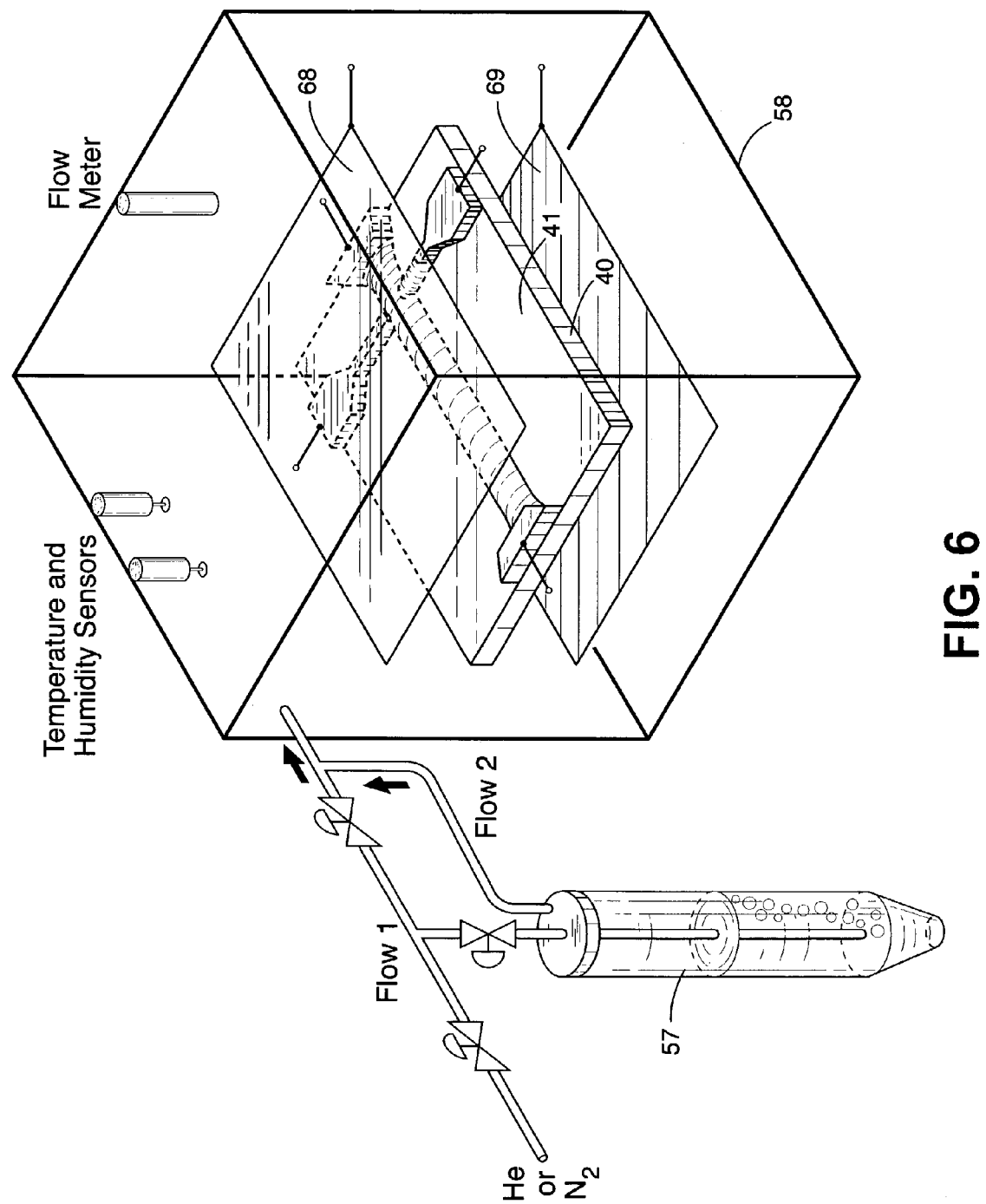
FIG. 6 is an illustration of a humidity control system that can be used to provide the humidity conditions required for use by some embodiments of the invention.

The controlled-humidity environment can be provided in a number of ways. For example, FIG. 6 presents one humidity-control system that can be used to provide the humidity conditions required for the formation of the micro/nanofluidic separation column 48. In the humidity control system of FIG. 6, the relative humidity is controlled by the ratio of the flow rate of a dry gas (flow 1) to the flow rate of a moisturized gas (flow 2). Ultra pure (water-free) helium or nitrogen gas can be used as the dry gas (flow 1). When the chamber 58 containing the single molecule separation and counting apparatus is purged 100% with this dry gas (flow 1), the relative humidity in the chamber will become zero. Bubbling the helium or nitrogen gas through a water bubbler 57, as illustrated in FIG. 6, will produce a moisturized gas (flow 2). Depending on the bubbling process efficiency and time, it is possible to saturate this moisturized gas with water vapor to 100% relative humidity. When the chamber 58 is purged with 100% of a vapor-saturated gas, the relative humidity in the chamber will reach its maximum (100% relative humidity). When the ratio of moisturized flow rate to the dry flow rate is in between, the value of relative humidity will be somewhere in between. Therefore, the relative humidity in the chamber 58 can be controlled by controlling the relative flow rates between the dry (flow 1) and moisturized (flow 2) gas. The thickness of the water or other liquid layer 48 that forms by vapor condensation on the strip of hydrophilic material 39 is controlled by the relative humidity and the properties of the hydrophilic surface 39 (FIGS. 4 and 5).

The inset view in FIG. 5 illustrates the micro/nanofluidic column 48 in cross section. The water (or other liquid) column 48 formed by condensation on the hydrophilic surface 39 has three distinct regions. These are (1) a stationary region 49 where water molecules are mostly bound with the hydrophilic surface 39; (2) a quasi-stationary region 50 which forms near the interface between the water column 48 and the gas phase because of water surface tension; and (3) a mobile region 51 in the middle of the water column, where water and sample molecules can move more freely.

When the thickness of the mobile water layer 51 is only about the size of the sample molecule 47, the sample molecule will touch the stationary region 49 of the nanofluidic column 48 as it moves through the column under the influence of an applied electrophoresis electric field. The electric field is provided by an electrophoresis pulse generator 63 (FIG. 7) that is connected across two electrophoresis macroelectrodes 54 and 55. Additional electric fields that are also used to further control molecule movement are described later. The contact that the sample molecules 47 make with the stationary water molecules 49 and/or the hydrophilic surface 39 generates drag forces that retard the movement of sample molecules 47 under the applied electric field. This retarding force is proportional to the mass, charge, and contact area of the sample molecule 47. Therefore, a separation of sample molecules 47 can be achieved by using the electrophoresis electric field and a thin layer of water or electrolyte solution 48. The micro/nanofluidic liquid layer 48 on the strip of hydrophilic surface 39 thus serves as a miniature pathway for the separation of single molecules.

For efficient-molecular separation, it is preferred to adjust the thickness of the mobile region 51 within the column 48 to roughly match the size of a given sample molecule as illustrated in the inset view in FIG. 5. For example, for separation of an aqueous $Mg^{2+}$ ion, which has an effective diameter of about 1.5 nm (including its bound and semi-bound water molecules), the thickness of the mobile water layer 51 of the column 48 should be adjusted to about 1.5–2 nm. For separation of a large molecule such as an isolated photosystem I reaction center (PSI), which has a size of about 6 nm, the thickness of the mobile water layer 51 should be adjusted to about 7–10 nm. This tuning can be achieved by controlling the ambient humidity as described above. Therefore, by adjusting the relative humidity, the thickness of the adsorbed water column 48 can be controlled. In addition, control of water adsorption, and thus the thickness of the water layer, can also be enhanced by using specific surfaces or chemically modified surfaces that include, but are not limited to $SiO_2$, SiN, and/or hydrogen-terminated Si surfaces. It is thus possible to obtain a water layer 48 with a thickness that is comparable to that of a sample molecule (such as that of a protein or a nucleic acid). Further, by modulating the relative humidity, the thickness of the water layer can be precisely manipulated.

The hydrophilic strip (surface) 39 that induces the formation of the micro/nanofluidic column 48 by water vapor condensation can be produced by a number of different micro/nanometer fabrication techniques. For example, the hydrophilic strip 39 can be produced by "drawing" the hydrophilic line, strip, or other pattern(s) on the hydrophobic surface 41. This drawing process can be achieved using photolithography with lasers or other micro/nanolithographic techniques. For example, a monolayer of hydrophobic molecules can be deposited on a substrate. Lines of these hydrophobic molecules can then be desorbed using a laser beam or atomic force microscopy (AFM) tip. The hydrophilic surface 39 can also be produced using contact printing technology. The width of these lines will be in the micron or nanometer range. By the use of nanoscale tools such as an AFM tip, hydrophilic lines of nanometer width can be created. Thus, it is possible to make hydrophilic lines of any shape on or in the hydrophobic surface 41 using simple lithographic techniques.

In the operation of the embodiment shown in FIGS. 4–7, a liquid solution that contains the sample molecules 47 to be separated is placed in the sample loading region 52. When a voltage difference is applied between the electrophoresis electrodes 54, 55 to create an electric field between them, the molecules move along the hydrophilic strip 39 toward the electrophoresis electrode 55. As the molecules move along the hydrophilic strip 39, they become separated. This is because, as described above, the thickness of the liquid column 48 is tailored to be comparable to the size of the sample molecules 47, causing the surface forces to retard the movement of the sample molecules under the applied electric field. This retarding force is proportional to the mass and charge of the molecule. Thus, the feeding and separation of the molecules 47 can be effectively achieved using an applied electrophoresis electric field and a thin layer of water or electrolyte solution as the micro- or nanofluidic column 48. As the separated sample molecules 47 move along the column and enter the nanoelectrode gate 42, they can be detected by the tunneling molecular detection means 65 and/or dielectric molecular detection means 66.

In FIG. 4, the fine-tuned detection gate 42 comprises the two precision nanotips 43, 44 of the nanoelectrodes 45 and 46 pointing toward each other on the nonconductive surface 41. The spacing (nanogap) between the two tips 43, 44 of the nanoelectrodes 45, 46 merely has to be sufficient (in a range of about 1–20 nm) for passage of individual molecules. For efficient passage and detection of a given sample molecule 47, an appropriate size for the detection gate must be chosen according to the specific size and physical properties of the sample molecule. For example, a nanogap as small as 1–3 nm should be chosen for passage and detection of a relatively small molecular species such as a $Mg^{2+}$ ion, which in aqueous solution may have a diameter of about 1.5 nm (including its bound water molecules). For larger molecules such as an isolated PSI complex, which has a size of about 6 nm, a larger nanogap (e.g., 7–10 nm) may be used. The specific requirement for nanogap size is also dependent on the temperature and liquid or solvent 48 conditions. To achieve the needed resolution for the detection of an individual molecule, the tips 43, 44 of the nanoelectrodes 45,46 must be relatively sharp. All of these requirements can be met by fine-tuning the nanogap size and utilizing especially sharp nanotips where needed. As described earlier, sharp nanotips can be achieved using the technique of programmable pulsed electrolytic metal deposition and depletion.

Figure 7:
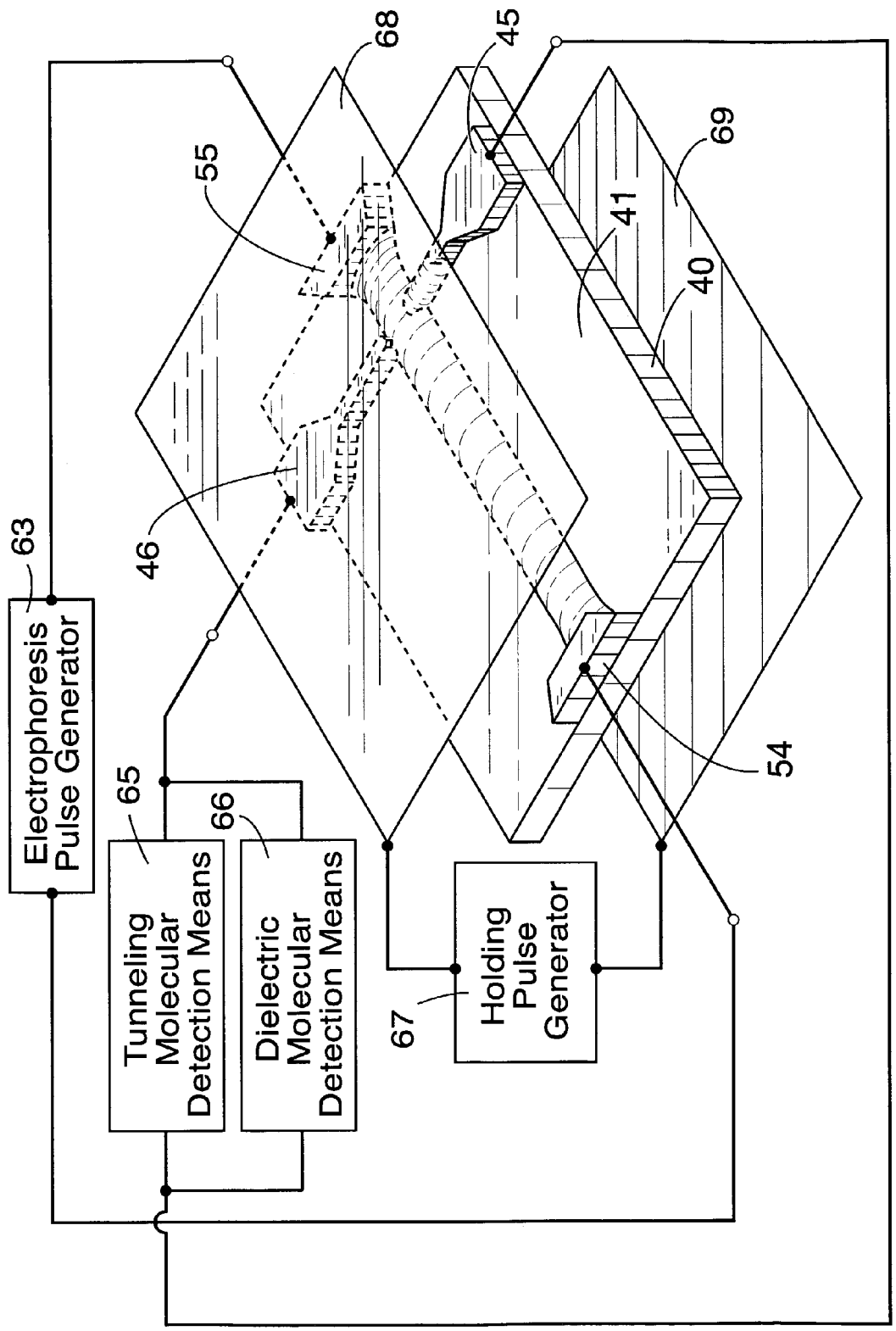
FIG. 7 is an illustration of the complete first embodiment of the invention for the separation, detection and counting of single molecules such as ions, proteins, nucleic acids, and charged particles and molecules.

In order to provide reliable detection and counting of single sample molecules 47, it is important to control the movement of the molecules. As illustrated in FIG. 7, two programmable, pulsed, and perpendicular electric fields are used. The first of these is the electrophoresis field, which is produced by a programmable pulse generator 63 connected to the pair of electrophoresis electrodes 54, 55. The second electric field is a holding electric field perpendicular to the substrate 40. It is produced by a second programmable pulse generator 67 connected to a pair of parallel conductive plates 68, 69 located on either side of the substrate 40, respectively.

Figure 13:
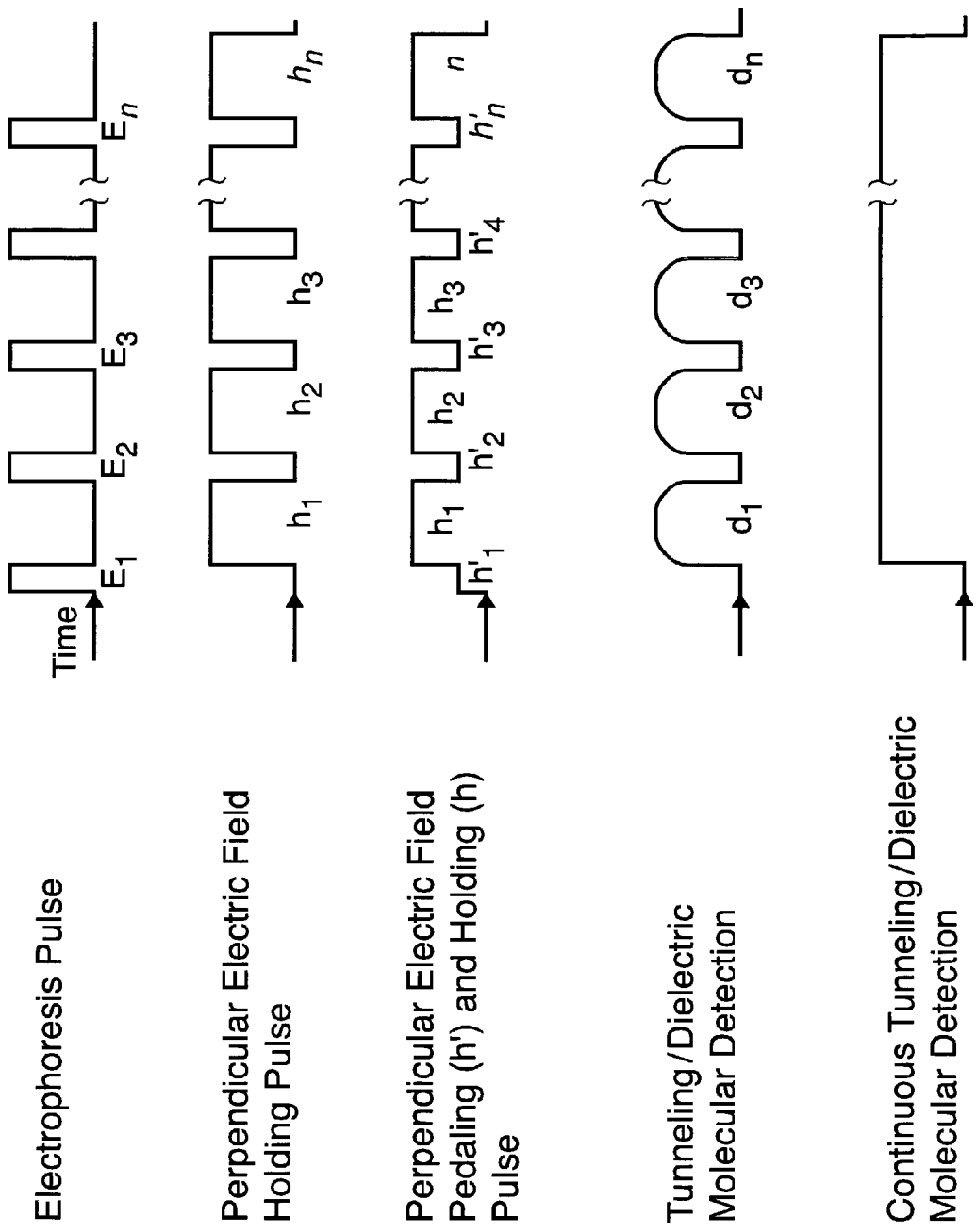
FIG. 13 is a graph illustrating one example of the synchronization and coordination of the electrophoresis electric field, the perpendicular holding electric field, and the molecular detection used in the invention.

Charged molecules can move under the influence of the electric fields. For example, ions that possess positive charges will move toward a cathode under the influence of the electric field. The step size of the molecular movement can be controlled by the duration and amplitude of the electrophoresis pulse. To provide sufficient time and stability for the nanoelectrodes 45, 46 to detect an individual molecule at the detection gate 42, the pulsed electrophoresis field is stopped for the detection period after the molecule enters the detection gate. To hold the molecule and to prevent any potential molecular drift, the holding electric field that is perpendicular to the substrate 40 is applied by the two parallel conductive plates 68, 69 located on either side of the substrate 40. Positively or negatively charged molecules can be retained on the surface of the substrate 40 when the plate 69 is charged negatively or positively, respectively. For example, with proper strength of the holding electric field between the conductive plates 68 (positively charged) and 69 (negatively charged), a positively charged species such as $Ca^{+2}$ can be held down on the surface of the substrate 40 steadily, as desired for tunneling and/or dielectric detection. This helps to achieve a reliable and reproducible detection of a molecular species. To achieve a coordinated process, the actions of the electrophoresis, perpendicular holding, and molecular detection may be synchronized as illustrated in FIG. 13.

Figure 8:
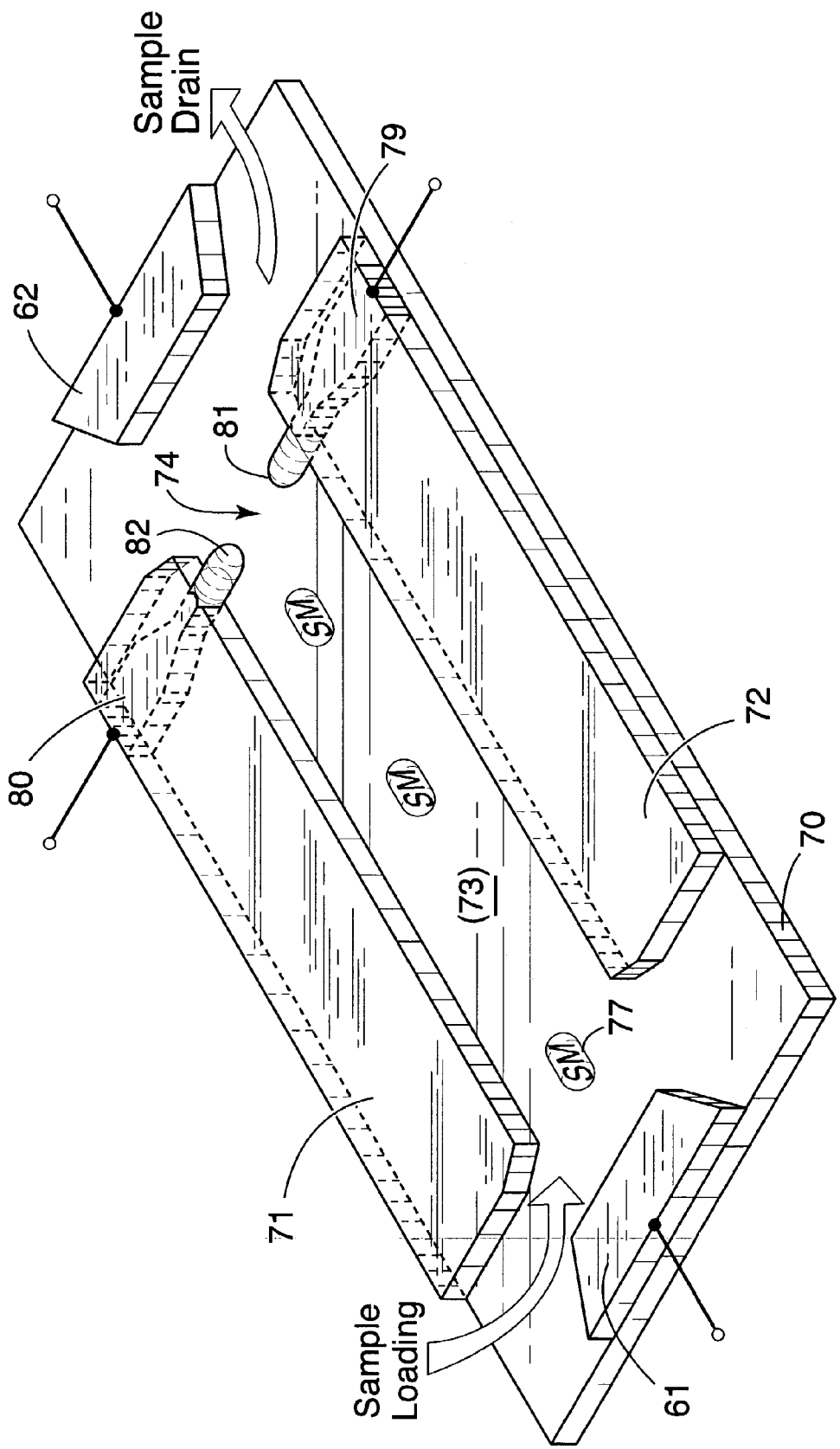
FIG. 8 illustrates a second embodiment of a molecular separation and counting system according to the invention, and features a nanofluidic trough constructed with nonconductive nonhydrophilic banks (e.g. SiN, or hydrogen-terminated Si surface) between electrophoresis electrodes on a nonconductive hydrophilic substrate (e.g., $SiO_2$).
Figure 9:
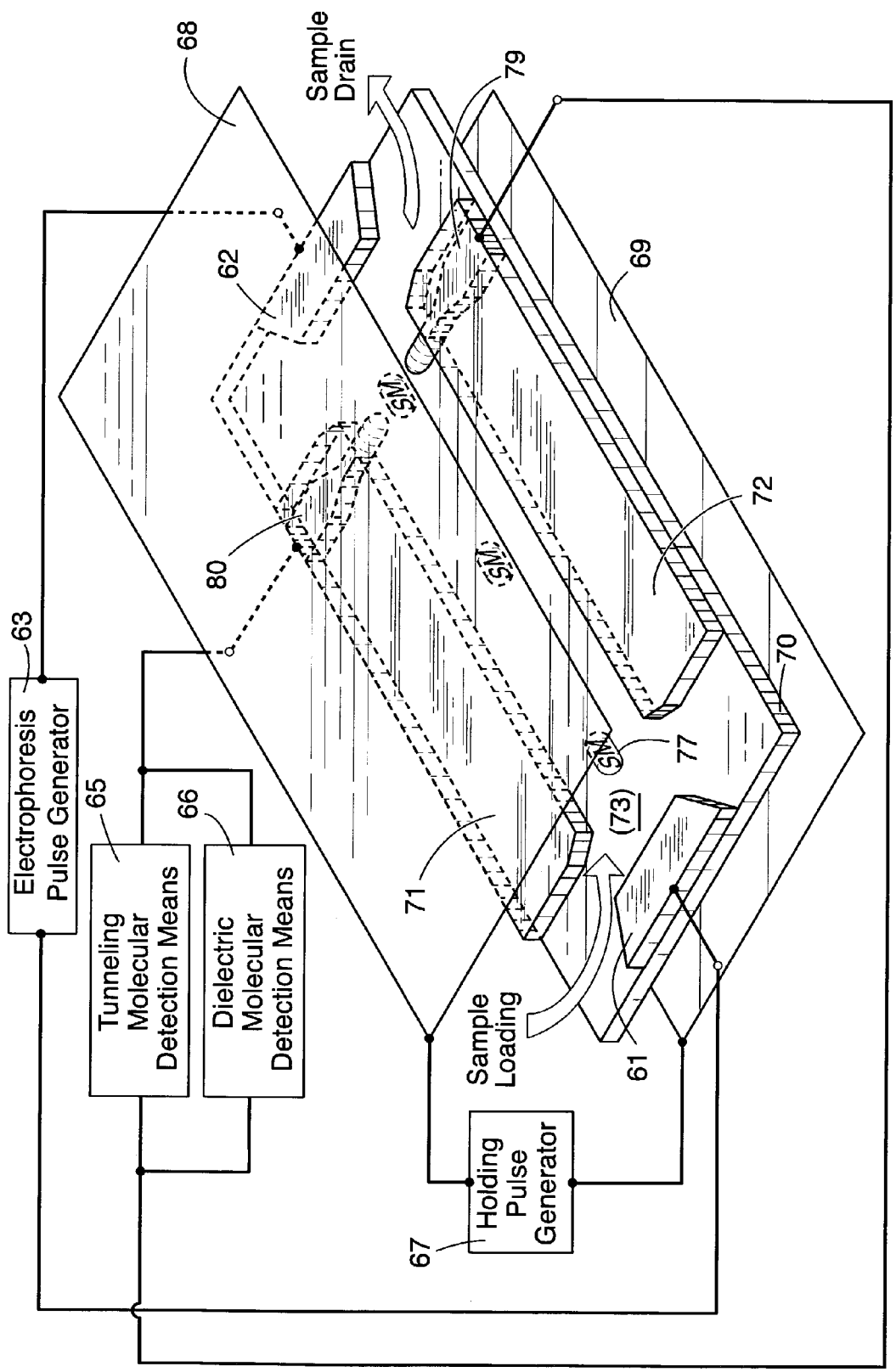
FIG. 9 is an illustration of the complete second embodiment of the invention for the separation, detection and counting of single molecules such as ions, proteins, nucleic acids, and charged particles and molecules.

A second embodiment of our invention is shown in FIGS. 8 and 9. Here, the separation and counting of single molecules 77 is achieved by electrophoresizing the sample molecules through a micro/nanofluidic separation trough 73, and by detecting the molecules at a nanometer-scale detection gate 74 through nanoelectrode-gated tunneling and dielectric measurements. In this embodiment, an AFM and/or EFM tip (not shown in FIGS. 8 or 9) can also be used at the nanometer gate as an optional means for molecular detection and/or counting.

In FIG. 8, the micro/nanofluidic separation trough 73 may be fabricated by affixing a hydrophobic nonconductive material 71 and 72 (such as SiN) to two selected portions of a hydrophilic substrate 70 (such as $SiO_2$). The hydrophobic nonconductive material 71, 72 acts as the banks or walls of the trough 73. The banks 71, 72 serve at least three different functions. They provide physical protection of the nanoelectrodes 79, 80 while making the nanoelectrode tips 81, 82 more rigid on the substrate. The banks also minimize the Faraday current leakage from the nanoelectrodes 79, 80, i.e., they electrically insulate, or shield, the sides of the nanoelectrodes from the Faraday leakage current. The third function the banks serve is that they help shape the trough for the liquid through the detection gate 74 for improved flow and separation of sample molecules, while preventing the sample molecules 77 from contacting the sides of the nanoelectrodes 79, 80.

In further detail, the banks 71, 72 can be fabricated using a combination of electron-beam lithography with polymethyl methacrylate (PMMA), shadow-mark sputtering deposition, ion-beam milling and pasting, and precision electrolytic deposition. Using such techniques, the width of the trough 73 can made as narrow as about 10 nanometers or as wide as desired. The length of the trough 73 can range from about 20 nm to millimeter scale. The other components of the second embodiment are the same as shown in the first embodiment, function the same as in the first embodiment, and are labeled the same. As with the first embodiment, this second embodiment of our apparatus is placed in a chamber (not shown) where the humidity can be controlled very accurately. The water vapor will condense in the trough 73 at certain levels of relative humidity. The thickness of the water layer (not shown in FIG. 8) depends on the relative humidity and temperature as before.

The sample loading and drain is the same as described previously, as are the means for producing the electrophoresis electric field and the holding electric field.

Figure 10:
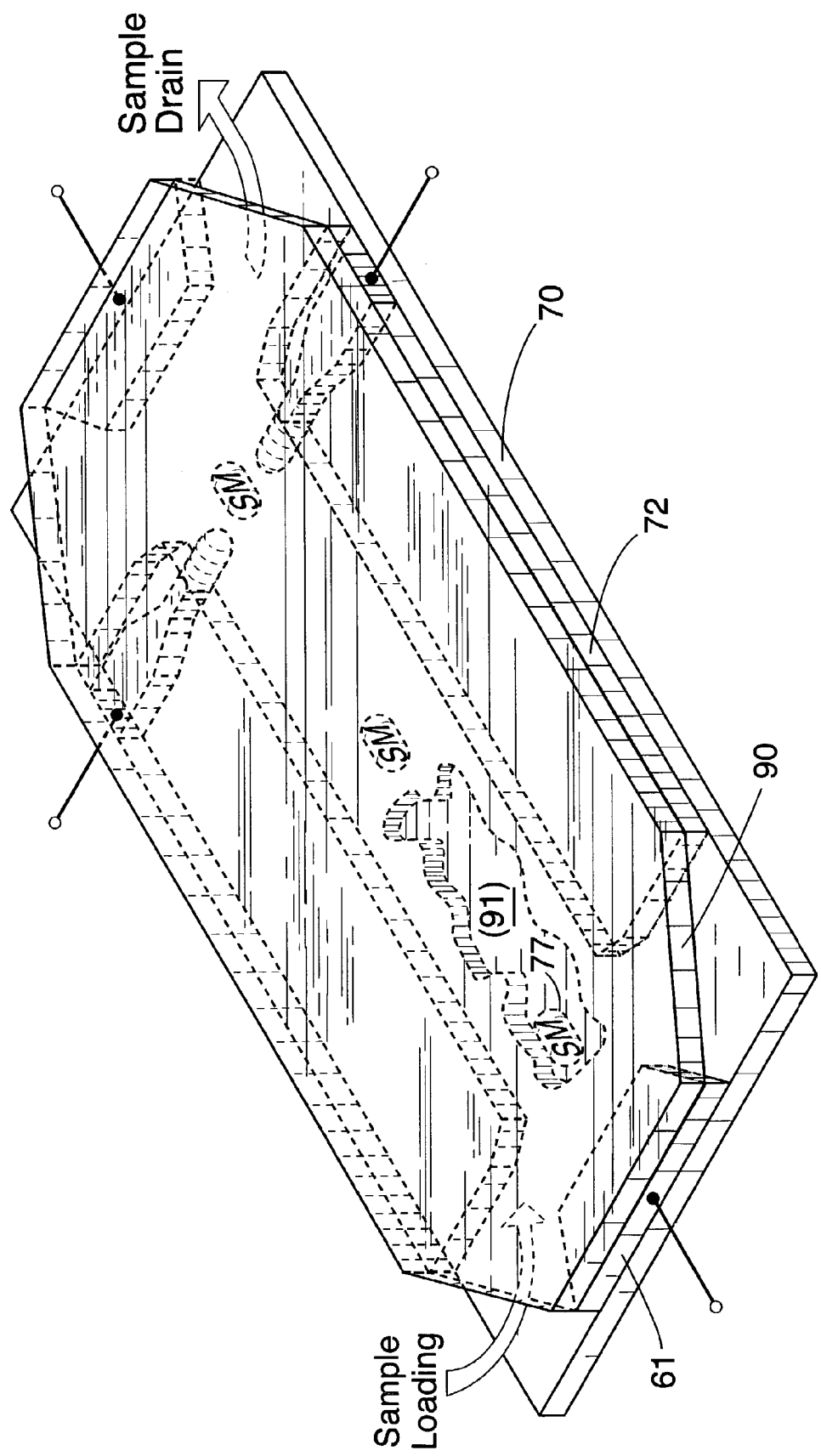
FIG. 10 illustrates a third embodiment of the invention. It features a covered nanofluidic passageway constructed with nonconductive banks (e.g. SiN, SiO$_2$) between electrophoresis electrodes on a nonconductive substrate, and a nonconductive cover on top of the molecular detection nanoelectrodes, electrophoresis electrodes, and the nonconductive banks.

A third embodiment of our invention is shown in FIG. 10. This embodiment slightly modifies the embodiment of FIGS. 8 and 9. The separation and counting of single molecules 77 is achieved by electrophoresizing the sample molecules as before, but utilizing a micro/nanofluidic covered passageway 91 for the liquid flow, and by detecting the molecules at a nanometer detection gate 74 through nanoelectrode-gated tunneling and dielectric measurements.

With reference to FIGS. 8–10, the modification is that of mounting a nonconductive cover 90 (FIG. 10) on the nanoelectrodes 79, 80, the nonconductive banks 71, 72, and the electrophoresis electrodes 61, 62. The mounting of cover 90 results in a confined space for the liquid sample loading near the electrode 61, a covered passageway 91 for the molecular separation, and sample drainage near the electrode 62. The covered passageway 91 allows the liquid and sample molecules to be transported from the sample loading area through the detection gate 74 to the sample drain area.

In this embodiment, the thickness of the liquid in the covered passageway 91 is controlled by the fixed height of the nonconductive banks 71, 72 and the cover 90 placed on the banks 71, 72 to form the covered passageway 91. Thus, in a manner similar to the previous embodiments, when the thickness of the sample-containing liquid is comparable to the size of the sample molecules, the liquid in the covered passageway 91 facilitates the molecular separation. It will be noted in this third embodiment with the covered passageway 91, that there is no need to provide the humidity control system because the height of the liquid is fixed.

The liquid, liquid with sample molecules, or sample molecules can be loaded in one side of the passageway 91 through the loading area shown in FIG. 10. Similar to the previous two embodiments, as the sample molecules 77 move through the passageway 91 toward the detection gate 74 under the influence of the electrophoresis electric field, they can be separated along the passageway 91 because they produce different dragging forces as they touch the hydrophilic plate 70 inside the covered passageway 91 owning to the difference in their charge, mass, and size. Also, as in the previous two embodiments, use of the pedaling electric field h' in conjunction with the electrophoresis electric fields, the molecular separation efficiency may also be improved. As they are separated and move through the detection gate 74, the sample molecules 77 are counted by the nanoelectrode-gated molecular detection means.

The detection and counting of single molecules in all embodiments of the our invention is achieved through the use of nanoelectrode-gated tip-to-tip electron tunneling conductance measurements 65, nanoelectrode-gated tip-to-tip electron tunneling spectroscopic measurements (also 65), and/or nanoelectrode-gated dielectric molecular detection 66. High-resolution atomic force microscopic (AFM) probing 78 and/or high-resolution electrostatic force microscopic (EFM) probing (also 78) are optional molecular detection means for embodiments I and II (FIGS. 4–9), but not for embodiment III (FIG. 10) where the detection gate is covered and not easily accessible to the AFM/EFM probe. The nanoelectrode-gated tunneling conductance spectroscopic measurement is described first.

In nanoelectrode-gated tunneling conductance spectroscopic measurements (FIG. 7) when the distance between the nanoelectrode tips 43, 44 is within about 10 nm, significant electron tunneling across the detection gate 42 can occur upon application of a biased tunneling voltage (V). When a sample molecule such as an ion (e.g., $Mg^{2+}$, $Ca^{2+}$, $[PO_4H]^{2-}$, or $[Fe(CN)_6]^{-3}$), protein, or nucleic acid molecule moves into the detection gate 42, the tunneling current will change because of the screening effect of a given molecule on the tunneling electrons. Since the chemical compositions and structures of the sample molecules are different, the screening effect of each distinct molecule on the tunneling current (I) and tunneling characteristics (such as the I-V and dI/dV-V curves) is likely to be different. For example, the I-V curve of an isolated PSI reaction center has quite unique diode-like characteristics along its axis pointing from the reaction-center pigment P700 to the terminal electron acceptor $F_{AB}$ at the reducing end of the complex [2, 3]. Therefore, it is possible to use tunneling-spectroscopic measurements to detect and count single molecules that pass through the detection gate 42.

Using some standard molecules of known identity, this detection system can be calibrated. A unique tunneling characteristic profile can then be established for each distinct sample molecule. This tunneling profile can then be used as a fingerprint to identify an individual molecule. Therefore, by detecting the difference in tunneling current (I) and tunneling characteristics (I-V and dI/dV-V curves) for each sample molecule 47 passing through the detection gate 42, the identification and counting of sample molecules can be achieved. With the ability to move a sample molecule 47 through the detection gate 42 in a well-controlled manner (by use of the electric fields described above), reliable detection and counting of single molecules can be obtained at high speed. Since the tunneling electrons likely emerge from a single (or a few) atom(s) of one nanoelectrode tip 43 and tunnel through the nanogate 42 to the other nanoelectrode tip 44 for the shortest possible distance, the size of the tunneling electron beam 56 (FIG. 4) is likely to be within a few angstroms (a fraction of a nanometer), which is sufficiently fine to allow precise detection and counting for a variety of molecular species including, but not limited to, ions (such as $Mg^{2+}$, $Ca^{2+}$, $[PO_4H]^{2-}$, and $[Fe(CN)_6]^{3-}$), nucleic acids, proteins, and charged particles and molecules.

The tip-to-tip tunneling current, I, between the nanoelectrodes can be expressed using Simmon's formula[1] as $$I = (3.16 \times 10^6) A \left[\frac{V}{S}\right] \sqrt{\phi} \cdot e^{(-1.025S\sqrt{\phi})}$$

where S is the distance between tips of the two nanoelectrodes in angstroms, V is the potential difference, A is the junction area, and $\phi$ is the work function. This formula shows the exponential decay of the electronic wave function at the metal vacuum interface. In liquids, this formula is not entirely accurate due to changes in work function, but it may be used as an approximation to aid the analysis of the tunneling process.

The applied potential, V, can be modified by the presence (or variation) of charge in the gap. Therefore, the presence of dielectric or charged materials in the gap can affect the tunneling current. This fact was observed by early researchers while imaging DNA molecules in solution using scanning tunneling microscopy (STM). Furthermore, the tunneling conductance can also be perturbed by the presence of conductive material, which could potentially, in effect, "shorten" the tunneling distance. A sample molecule such as a protein can not only be a dielectric species that contains certain molecular partial charge; it may also possess certain conductivity for electron transport. When such a sample molecule enters the detection gate between the two sharp nanoelectrode tips, its molecular partial charge could effectively change the potential difference from V to V+ΔV and its conductivity would, in effect, "shorten" the tunneling distance S by ΔS. Therefore, the tunneling current I is expected to change as a result of the perturbation (ΔV and ΔS) on V and S caused by the presence of a sample molecule at the detection gate. This explains why a sample molecule with a distinct chemical composition and structure can produce a specific perturbation effect on the tunneling properties and why it can be detected by measuring its perturbation effect on the tip-to-tip tunneling properties when it enters a nanometer detection gate.

As described above, and with reference to FIG. 7, the sample molecule transport is controlled by the two perpendicular electric fields provided by the pair of macroelectrodes 54, 55, and the pair of conductive plates 68, 69 with pulsed DC voltage. Because of this, it is better to apply an AC voltage rather than a DC voltage between the nanogap electrodes 45, 46 for tunneling perturbation measurement. This will minimize the effect of DC voltage used for control of sample molecule movement on the sensing current measured across the nanogap. Therefore, the current I in Simmon's equation above is preferably an alternating current. Since the frequency of the input AC voltage (V) can be in a megahertz (MHz) range, the detection of a sample molecule by nanoelectrode-gated tunneling perturbation monitoring can be completed within a microsecond. By use of the programmable electric fields described above, it is possible to move a sample molecule through the detection gate 42 at a speed as fast as about one molecule per nanosecond. Therefore, this nanotechnology-based molecular counting system can have a theoretical maximal counting rate of about 1,000,000 molecules per second per detection gate.

Furthermore, this nanoelectrode-gated tunneling perturbation detection system offers at least two additional advantages over a conventional STM system with regard to the detection and/or counting of single molecules. First, the tip-to-tip tunneling electron beam 56 across a pair of sharp nanoelectrode tips 43, 44 is likely to be more focused (sharper) than a STM tunneling beam that operates from a tip to a conductive plate (plane). Therefore, in a tip-to-tip geometry, the nanoelectrode-gated detection/counting system potentially has a higher sensitivity than that of the tip-to-plane geometry. Second, in STM, by design and because of mechanical noise, the tip-to-substrate distance often varies between experiments. In our tunneling molecular detection/counting system, only a single molecule moves through the detection gate at a time. The distance between the two nanoelectrode tips (after being fine-tuned for optimized detection sensitivity) is constant, permitting more-reproducible tunneling molecular detection/counting to be achieved.

The detection and counting of single molecules by means of nanoelectrode-gated dielectric characterization is now described. Again in FIG. 7, when the tips 43, 44 of the two nanoelectrodes 45, 46 are placed in close proximity, they can act as a nanocapacitor (75 in FIG. 11). The capacitance of this nanocapacitor is dependent on the dielectric constant of the molecule and liquid 48 between the two nanoelectrodes 45, 46. Sample molecules have different structures and compositions. Therefore, the dielectric constants of these molecules may vary. For example, the dielectric constants for organic materials such as proteins and nucleic acid are typically about 2–4, which is a factor of about 20–40 times smaller than that of free water (dielectric constant: 80). Therefore, large organic molecules such as proteins and nucleic acids can be detected quite easily in an aqueous background by use of this dielectric detection method.

Another factor contributing to differences in the dielectric constant measurement is the interaction between the sample molecule 47 and the liquid 48 molecules (water or solvent, for example). Some water molecules are "bound or semi-bound" around certain sample molecules such as a $Mg^{2+}$ ion and the negatively charged phosphate groups of a DNA molecule. These water molecules have less freedom for rotation and are thus less polarizable than the free water molecules in a bulky phase. Consequently, the dielectric constant of the bound or semibound water molecules is significantly smaller than that of free water molecules. The more bound water molecules an ionic species can have, the more distinct dielectrically it can be in comparison with the bulky aqueous background (free water molecules). Therefore, higher-valent ions such as $Mg^{2+}$, $Ca^{2+}$, $[PO_4H]^{2-}$, and $[Fe(CN)_6]^{3-}$, which can have more bound water molecules, are generally more detectable via dielectric monitoring than are one-valent ions such as $Na^+$ or $Cl^-$.

Figure 11:
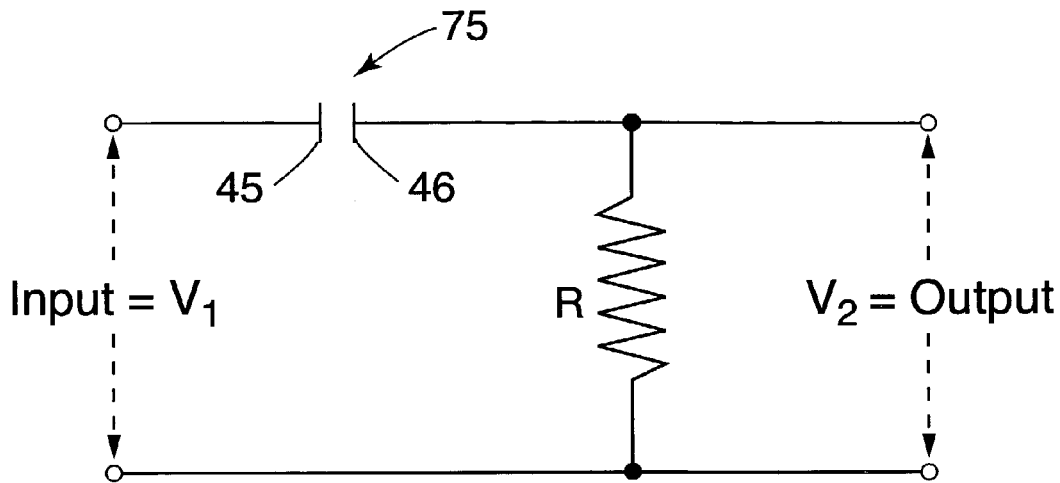
FIG. 11 is a circuit used for molecular detection by nanoelectrode-gated dielectric measurement.
Figure 12:
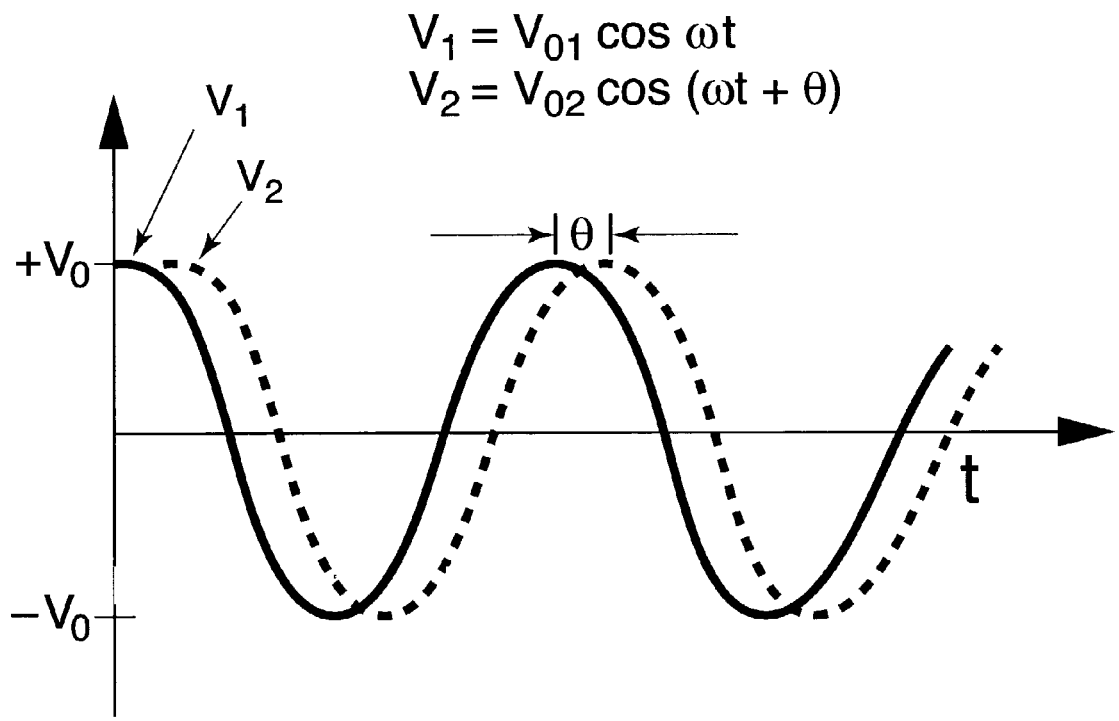
FIG. 12 is a graph illustrating the phase shift θ between the input AC voltage $V_1$ and the output voltage $V_2$ from the circuit of FIG. 10 used to detect sample molecules.

The difference in the value of the dielectric constant can be translated into a difference in the capacitance for the nanoelectrodes 45, 46 if the tips of the nanoelectrodes are sharp enough and within an appropriate distance (nanometer range) of the sample molecule 47. With an electronic circuit as shown in FIG. 11, it is possible to detect the difference in capacitance by measuring the phase shift ($\theta$) between an input ac voltage ($V_1$) and an output voltage signal ($V_2$). This is because the phase shift is a function of the capacitance (C) at a proper ac frequency ($\omega$) and impedance (R):

$$\theta = \tan^{-1}(1/\omega RC).$$

By using some molecules of known identity, calibration of this detection system is possible. A unique phase-shift profile can be established for each distinct molecule. This profile can then be used as a "fingerprint" to identify an individual molecule. With the ability to move a molecule through the detection gate 42 in a well-controlled manner as described above, reliable detection and counting of single molecules can be accomplished.

Besides the tip-to-tip tunneling perturbation measurement 65 and the nanoelectrode-gated dielectric measurement 66, atomic force microscopy (AFM) and electrostatic force microscopy (EFM) probing (both illustrated at 78 in FIG. 5) are additional methods for detection of sample molecules that can be used with this invention. As illustrated in FIG. 5, when a funnel-column-like nanometer (1- to 20-nm) water layer 48 is used, the entire process, including sample loading, separation, and delivery of sample molecules to the detection gate for detection and/or counting of single molecules, can be carried out on the surface of the substrate 40. In this open configuration, an optional molecular detection probe such as a sharp AFM or EFM tip 78 can be easily added in or above the nanometer water layer at the nanoelectrode detection gate 42.

The AFM probing can be used to determine whether a sample molecule is present. An AFM tip that is sufficiently fine (such as one made of a carbon nanotube) may be able to detect certain characteristic differences between different and big sample molecules. However, conventional AFM imaging so far has not been able to resolve individual molecular structures. Thus, at present, AFM probing can aid in molecular detection or counting, but would not be sufficient to obtain complete molecular identification. In the use of this part of the invention, the tapping mode of AFM operation may be preferred to ensure that no undesirable drag of the molecule by the AFM tip occurs.

A time-dependent probing profile can be obtained by using the AFM tip 78 to scan on top of the sample molecule 47 back and forth in the nanoelectrode 45, 46 direction while the sample molecule moves through the detection gate in the macroelectrode 61, 62 direction during the pulsed electrophoresis. When the speed of the sample movement under a given electrophoresis electric field is known, an image file can be reconstructed from the time-dependent AFM probing files.

The velocity of the sample molecule transport during the electrophoresis period can be determined by comparative analysis of the time-dependent profile with standard AFM images that can be obtained while the molecule is held steadily at the gate by the holding electric field. The velocity information can be useful in adjusting the strength and duration of the electrophoresis electric field to achieve the desired speed of the molecular movement for the detection and/or counting of the sample molecules. The detection system can be calibrated with some standard molecules of known identity. A characteristic AFM probing profile can be established for certain standard molecular species of interest. This type of profile can then be combined with the tip-to-tip tunneling perturbation and other detection profiles, and become an aid to the detection and/or counting of single molecules.

As mentioned above, FIG. 5 also illustrates that a sample molecule can be detected or counted with EFM probing. Certain sample molecules or species (such as $Mg^{2+}$, $Ca^{2+}$, $[PO_4H]^{2-}$, and $[Fe(CN)_6]^{3-}$) contain certain surface charges. The addition of acid or alkali to the water layer 48 can ionize certain groups of certain molecular species such as proteins and nucleic acids. The charge density of some species may differ at certain pH conditions. Therefore, the use of EFM probing can potentially help to identify the molecular species. The objective is to obtain some distinct signals from the EFM probing that can be used to detect and/or count the sample molecules. EFM probes having a sharp tip that is doped with a single-charged atom are now available. This type of EFM tip should have a resolution that is sufficiently fine to probe single molecules. Preferably, the EFM probing should be operated in the tapping mode to achieve optimal detection sensitivity.

In the practice of our invention, control of the liquid 48 conditions and electric fields is necessary to enhance the separation and detection of single molecules. Different sample molecules may have somewhat different $pK_a$ values or different affinities to certain solvent molecules. It should be possible to make certain sample molecules more separable and/or more detectable by controlling the solvent 48 conditions. For example, by adjusting the pH of the solvent, it should be possible to ionize only certain sample molecules so that they can be more readily separated and/or detected through the nanofluidic column 48 and the nanometer gate 42 described in this invention.

It is also possible to enhance the molecular separation by use of a biased holding electric field during the process of electrophoresis. This is done to make the sample molecules 47 interact with the stationary hydrophilic surface 39 in a somewhat different manner so that they can become more easily separated in the separation process. For example, during electrophoresis, a DNA molecule that contains negatively charged chains of phosphate groups can be "pedaled" down to the hydrophilic surface 39 by use of a biased holding electric field (h' in FIG. 13) that is generated when the conductive plate 69 beneath the substrate 40 is positively charged. This pedaling action will cause the sample molecules to contact the stationary surface 39 with greater force. Individual molecules may show differences in this enforced interaction with the surface 39 because of their variations in molecular rigidity, charge, polarity, and surface properties. Any variations among sample molecules in this forced interaction with the stationary surface may generate different amounts of the surface-retarding force. As a result, this pedaling action may make some of the sample molecules become more separable in this nanofluidic separation process. The degree and direction of the pedaling actions can be manipulated by controlling the amplitude and polarity of the pedaling electric field h'.

It may be desirable to integrate the molecule separation and counting process through computerized system control and data acquisition. In order to achieve the optimal performance of this invention, multiple detection gates may be used in serial and/or in parallel so that all or any combinations of the molecular separation and detection techniques described herein can be employed. The actions of the perpendicular electric field and the molecular detection processes can be coordinated through computerized system control and data acquisition. A characteristic profile of the probing signals can be established for each distinct sample molecule by subjecting the molecules of known identity to one or all of the detection techniques described above. These characteristic signal profiles can then be used to identify the sample molecules by means of computer data fitting. A number of different sample molecules 47 can therefore be counted one by one as each of them passes through the detection gate 42.

The various parts of the invention including the three embodiments, separation of sample molecules by electrophoresizing through micro/nanofluidic columns, troughs and covered passageways, nanoelectrode-gated molecular detection, and the process control and enhancement may be applied in full, in part, or in any combination. The methods for the detection of single molecules including the nanoelectrode-gated tunneling conductance spectroscopic measurements, nanoelectrode-gated dielectric characterization, and AFM/EFM probing may be applied in full, in part, or in any combination. One and/or multiple pairs of detection nanoelectrodes 45, 46 may be applied in serial and/or in parallel to further enhance the performance of this invention.

While there has been shown and described what are at present considered the preferred embodiments of the invention, it will be obvious to those skilled in the art that various changes and modifications can be prepared therein without departing from the scope of the inventions defined by the appended claims.

We claim:

1. An apparatus for the separation and counting of sample molecules in a liquid comprising:
   a) a nonconductive hydrophobic base;
   b) a pair of macroelectrodes located on said base;
   c) a strip of hydrophilic material for accommodating the liquid, said strip of hydrophilic material located on said nonconductive hydrophobic base between said macroelectrodes;
   d) a pair of nanoelectrodes located on said base crosswise of said strip of hydrophilic material, the gap between said nanoelectrodes forming a nanoscale detection gate, the nanoscale detection gate located in the liquid;
   e) a programmable pulse generator connected to produce an electrophoresis electric field between said macroelectrodes, the electrophoresis electric field capable of controllably moving sample molecules in the liquid along said strip of hydrophilic material through the detection gate;
   f) a pair of parallel spaced-apart electrically conductive plates, said base located between said parallel spaced-apart electrically conductive plates;
   g) a second programmable pulse generator connected to produce a holding electric field between said electrically conductive plates, the holding electric field capable of holding and/or orienting sample molecules in the liquid with respect to said base; and
   h) a molecule detection means connected to said nanoelectrodes.

2. The apparatus of claim 1 wherein said strip of hydrophilic material has an expanded portion for use as a sample molecule loading or drainage area, said expanded portion located proximate to one or both of said macroelectrodes.

3. The apparatus of claim 1 wherein the level of the liquid is maintained by a controlled humidity environment and the hydrophilic property of said strip of hydrophilic material.

4. The apparatus of claim 1 wherein said molecule detection means is a nanoelectrode-gated tip-to-tip electron tunneling conductance monitoring system.

5. The apparatus of claim 1 wherein said molecule detection means is a nanoelectrode-gated tip-to-tip electron tunneling spectroscope.

6. The apparatus of claim 1 wherein said molecule detection means is a nanoelectrode-gated dielectric molecular detector.

7. The apparatus of claim 1 further comprising a high-resolution atomic force microscopic probe.

8. The apparatus of claim 1 further comprising a high-resolution electrostatic force microscopic probe.

9. The apparatus of claim 1 further comprising a sample molecule loading device.

10. The apparatus of claim 9 wherein said sample molecule loading device is a liquid sample loading device.

11. The apparatus of claim 10 wherein said liquid sample loading device is a micropipette.

12. The apparatus of claim 10 wherein said liquid sample loading device is a microfluidic injection device.

13. The apparatus of claim 10 wherein said liquid sample loading device is a nanofluidic injection device.

14. The apparatus of claim 1 wherein the movement and orientation of sample molecules in the liquid is precisely controlled by coordinated action of the electrophoresis electric field and the holding electric field.

15. The apparatus of claim 1 wherein the moving direction and step size of a sample molecule at said detection gate is controlled by adjusting the direction, amplitude, and duration of the electrophoresis electric field.

16. The apparatus of claim 1 wherein a sample molecule in the liquid is oriented with its charged domain pointing in a preferred direction by the holding electric field at the proper strength and in the correct direction.

17. The apparatus of claim 1 wherein a sample molecule is held at said detection gate for a period of time by an electric pulse from said second programmable pulse generator, the electric pulse delivered through said parallel electrically conductive plates to ensure reliable detection and/or counting of the sample molecule.

18. The apparatus of claim 1 wherein the passage of a single sample molecule is achieved by use of detection gate spacing in the range of 1–20 nm.

19. The apparatus of claim 1 wherein the detection of a single sample molecule is achieved by use of detection gate spacing in the range of 1–20 nm.

20. The apparatus of claim 1 wherein the separation and transport of the sample molecules through said strip of hydrophilic material and through the detectiop gate is achieved by electrophoresizing the sample molecules through said strip of hydrophilic material in coordination with the holding electric field.

21. The apparatus of claim 1 wherein the passage and detection and/or counting of single sample molecules is enhanced by use of appropriate solvent conditions such as pH and ionic strengths.

22. The apparatus of claim 1 wherein the actions of the electrophoresis electric field, holding electric field, and the molecular detection and/or counting are coordinated and synchronized.

23. The apparatus of claim 1 wherein said apparatus is calibrated with standard molecules of known identity and signal profiles of standard molecules are established for each distinct molecule of interest.

24. The apparatus of claim 1 wherein the identity of an unknown sample molecule is determined by comparing its detection signal profile with the established signal profiles of standard molecules using computer-assisted data fitting.

25. An apparatus for the separation and counting of sample molecules in a liquid comprising:
a) a hydrophilic base;
b) a pair of macroelectrodes located on said base;
c) a trough produced by two parallel strips of hydrophobic nonconductive material on said hydrophilic base, said trough located between said macroelectrodes;
d) a pair of nanoelectrodes located on said base crosswise of said trough, the gap between said nanoelectrodes forming a nanoscale detection gate, the nanoscale detection gate located in the liquid;
e) a programmable pulse generator connected to produce an electrophoresis electric field between said macroelectrodes, the electrophoresis electric field capable of controllably moving sample molecules in the liquid along said trough through the detection gate;
f) a pair of parallel spaced-apart electrically conductive plates, said base located between said parallel spaced-apart electrically conductive plates;
g) a second programmable pulse generator connected to produce a holding electric field between said electrically conductive plates, the holding electric field capable of holding and/or orienting sample molecules in the liquid with respect to said base; and
h) a molecule detection means connected to said nanoelectrodes.

26. The apparatus of claim 25 wherein said nanoelectrodes are encased in said parallel strips except for the nanoelectrode tips.

27. The apparatus of claim 25 wherein the level of the liquid is maintained by a controlled humidity environment and the hydrophilic property of said trough.

28. The apparatus of claim 25 wherein said molecule detection means is a nanoelectrode-gated tip-to-tip electron tunneling conductance monitoring system.

29. The apparatus of claim 25 wherein said molecule detection means is a nanoelectrode-gated tip-to-tip electron tunneling spectroscope.

30. The apparatus of claim 25 wherein said molecule detection means is a nanoelectrode-gated dielectric molecular detector.

31. The apparatus of claim 25 further comprising a high-resolution atomic force microscopic probe.

32. The apparatus of claim 25 further comprising a high-resolution electrostatic force microscopic probe.

33. An apparatus for the separation and counting of sample molecules in a liquid comprising:
a) a hydrophilic base;
b) a pair of macroelectrodes located on said base;
c) a covered passageway produced by two parallel strips of hydrophobic nonconductive material on said hydrophilic base and a nonconductive cover on said parallel strips of hydrophobic nonconductive material, said covered passageway located between said macroelectrodes;
d) a pair of nanoelectrodes located on said base crosswise of said covered passageway, the gap between said nanoelectrodes forming a nanoscale detection gate, the nanoscale detection gate located in the liquid;
e) a programmable pulse generator connected to produce an electrophoresis electric field between said macroelectrodes, the electrophoresis electric field capable of controllably moving sample molecules in the liquid along said covered passageway through the detection gate;
f) a pair of parallel spaced-apart electrically conductive plates, said base located between said parallel spaced-apart electrically conductive plates;
g) a second programmable pulse generator connected to produce a holding electric field between said electrically conductive plates, the holding electric field capable of holding and/or orienting sample molecules in the liquid with respect to said base; and
h) a molecule detection means connected to said nanoelectrodes.

34. The apparatus of claim 33 wherein the thickness of the liquid is fixed by the height of said covered passageway and the properties of its inside walls.

35. The apparatus of claim 33 wherein said nanoelectrodes are encased in said parallel strips except for the nanoelectrode tips.

36. The apparatus of claim 33 wherein said molecule detection means is a nanoelectrode-gated tip-to-tip electron tunneling conductance monitoring system.

37. The apparatus of claim 33 wherein said molecule detection means is a nanoelectrode-gated tip-to-tip electron tunneling spectroscope.

38. The apparatus of claim 33 wherein said molecule detection means is a nanoelectrode-gated dielectric molecular detector.

* * * * *